(12) United States Patent
Laufer

(10) Patent No.: US 8,623,015 B2
(45) Date of Patent: *Jan. 7, 2014

(54) METHODS AND DEVICES FOR REMOVING OMENTAL TISSUE

(75) Inventor: Michael D. Laufer, Menlo Park, CA (US)

(73) Assignee: Lenr, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/473,388

(22) Filed: May 16, 2012

(65) Prior Publication Data

US 2013/0018363 A1    Jan. 17, 2013

Related U.S. Application Data

(63) Continuation of application No. 12/575,282, filed on Oct. 7, 2009, now Pat. No. 8,206,386.

(60) Provisional application No. 61/103,244, filed on Oct. 7, 2008.

(51) Int. Cl.
*A61B 18/14*    (2006.01)

(52) U.S. Cl.
USPC .................... 606/49; 606/41; 128/898

(58) Field of Classification Search
USPC ................. 606/27, 41, 45–52; 128/898
See application file for complete search history.

(56) References Cited

U.S. PATENT DOCUMENTS

| | | | |
|---|---|---|---|
| 4,534,347 A * | 8/1985 | Taylor | 606/33 |
| 5,382,231 A * | 1/1995 | Shlain | 128/898 |
| 6,032,673 A * | 3/2000 | Savage et al. | 128/898 |
| 6,663,639 B1 * | 12/2003 | Laufer et al. | 606/139 |
| 2006/0259035 A1 * | 11/2006 | Nezhat et al. | 606/50 |

* cited by examiner

*Primary Examiner* — Michael Peffley
(74) *Attorney, Agent, or Firm* — Levine Bagade Han LLP

(57) ABSTRACT

The invention relates to a method of treating obesity, insulin resistance and co-morbidities of these conditions by removing tissue from the abdomen. More specifically, it relates to a method of removing abdominal fat and omentum to which the fat is attached, in order to improve health. The invention includes a device for safely removing this tissue material.

24 Claims, 6 Drawing Sheets

METHODS AND DEVICES FOR REMOVING OMENTAL TISSUE

RELATED APPLICATIONS

This application is a continuation of U.S. patent application Ser. No. 12/575,282, filed Oct. 7, 2009, issued U.S. Pat. No. 8,206,386, which claims the benefit of U.S. Provisional Application No. 61/103,244, filed Oct. 7, 2008. The contents of which are incorporated herein by reference in their entirety.

BACKGROUND OF THE INVENTION

1. Field of the Invention

The invention relates to a method of treating obesity, insulin resistance and co-morbidities of these conditions by removing tissue from the abdomen. More specifically, it relates to a method of removing abdominal fat and omentum to which the fat is attached, in order to improve health. The invention includes a device for safely removing this tissue material.

2. Brief Description of the Related Art

The number of obese and morbidly obese people in the US has grown to 70 million in 2006, of which 10 million are morbidly obese (BMI>40). It is expected that this number will grow to 90 million by 2012. Along with direct deleterious effects, obesity also gives rise to other co-morbidities, the most significant being Type II diabetes (24 million in the US, an increase from 12 million 10 years ago), heart and circulatory disease, including peripheral vascular and stroke.

As discussed below, it is believed that there is a direct connection between abdominal fat and type II diabetes. Although obesity and abdominal fat are closely linked, the ratio between abdominal fat and other body fat is a more important indicator of type II diabetes and other morbidities from hormonally-active fat.

Conventional methods for treating obesity include drugs, dieting and surgery. For many patients, short term dietary changes do not result in long term weight loss. This leads many patients to select surgery, especially those patients with significant morbidity related to obesity. In 2004, the Centers for Medicare & Medicaid Services ("CMS") decided to reimburse bariatric surgery. This decision contributed to an already fast-growing rate of obesity surgery: up from 19,000 in 1998 to over 220,000 in 2006. Average reimbursement per case is approximately $25,000, with significant additional expense to treat follow-on issues, such as infection and gastric problems.

Current methods and devices for removing omentum and fat require either open surgery with large incisions or can be done with difficulty using laparoscopic techniques. However, the current procedures require painstaking cauterization of the blood vessels contained within this tissue material and careful excision. Frequently, the procedure is complicated by bleeding in the area of the tissue removal, requiring prolonged hospitalization and/or reoperation. The complications from bleeding limit the procedure to rare occasions and is only performed by particularly skilled surgeons.

Omentectomy (removal of the omentum and fat) is currently reimbursable but not often done. This may be due in part to the complexity and surgical risks inherent in these operations. These are compounded by the need for prolonged general anesthesia and immobility before and after the surgery.

Removing omental fat from the middle of the abdomen is significant in at least two ways: (1) omental fat is a primary contributor to Type II diabetes, and (2) omental fat contributes to coronary artery disease and other co-morbidities of obesity. Even moderately obese patients with larger abdominal girth are at higher risk for comorbidities like hypertension, diabetes and arterial vascular disease. Abdominal fat remains behind even after significant weight loss and continues to add risk to these patients. Only by removing this abdominal fat can these problems be directly addressed. Abdominal fat is the single largest factor in determining insulin resistance and an atherogenic lipid profile. It is believed that removing abdominal fat can reduce both diabetes (due to insulin resistance) and arterial sclerosis (due to lipogenic atheroma). Reducing arterial sclerosis can lead to a reduction of stroke, hypertension and peripheral arterial disease.

It has been found in a number of human studies that the presence of omental fat has a higher correlation with the production of dyslipidemia, hypertension, congestive heart failure and inflammatory response than the usual measures of obesity, such as BMI (Body Mass Index).

This correlation has been established by substantial animal testing, epidemiological studies relating visceral (omental) fat with metabolic, hormonal and vascular disorders, and with Type II diabetes. There are a number of studies currently underway, but the largest study compared bariatric surgery (Lap Band) with bariatric surgery and omentum removal (A Thörne, 2002). This study was performed on 50 patients. While all received an adjustable gastric band (AGB) for gastric reduction, half (n=25) additionally had a portion of their fatty omentum removed. The total amount removed was small—only 0.8% of total body fat (which amounts to only about 1 pound for a 300-pound person with a BMI of 40). 2 Despite the relatively small amount of fat removed, the omentectomized patients recorded significant reductions in oral glucose tolerance and insulin sensitivity—2 to 3 times greater than control subjects (P=0.009 to 0.04). The authors concluded:

Omentectomy, when performed together with AGB, has significant positive and long-term effects on the glucose and insulin metabolic profiles in obese subjects (A Thörne, 2002).

Multiple published articles are included in this application and are included here by reference. A Thörne, F Lönnqvist, J Apelman, G Hellers and P Amer. "A pilot study of long-term effects of a novel obesity treatment: omentectomy in connection with adjustable gastric banding." International Journal of Obesity 26.2 (2002): 193-199; Adams, M. The truth on losing abdominal body fat—forget the diet hype, here's how it really works. 18 Apr. 2005. 24 Sep. 2008 <<http://www.naturalnews.com/z006981.html>>; Brochu, M, Starling, R D, Tchernof, A, Matthews, D E, Garcia-Rubi, E and Poehlman, E T. "Visceral Adipose Tissue Is an Independent Correlate of Glucose Disposal in Older Obese Postmenopausal Women." The Journal of Clinical Endocrinology & Metabolism (2000): 2378-2384; Brower, B G, Visseren, F L J, Stolk, R P and van der Graaf, Y; "Abdominal Fat and Risk of Coronary Heart Disease in Patients with Peripheral Arterial Disease*." Obesity (2007): 1623-1630; Cid Pitombol, Eliana P Aranjo, Claudio T De Souza, José C Pareja, Bruno Geloneze and Lício A Velloso. "Amelioration of diet-induced diabetes mellitus by removal of visceral fat." Journal of Endocrinology (2006): 699-706; C V Ferchak, L F Meneghini. "Obesity, bariatric surgery and type 2 diabetes—a systematic review." Diabetes Metabolism Research and Reviews (2004): 438-445; Despres, J-P, Lemieux, I, Prud'homme, D. "Treatment of obesity: need to focus on high risk abdominally obese patients." British Medical Journal (2001): 716-720; Flegal K, Carroll M, Kuczmarski R, et al. "Overweight and obesity in the United States: prevalence and trends, 1960-1994." Int J Obes Relat Metab Dis. (1998): 39-47; Gabriely, I, Ma, X H, Yang, X M, Atzmon, G, Rajala, M W, Berg, A H, Scherer, P, Rossetti, L and Barzlai, N. "Removal of Visceral Fat Prevents Insulin Resistance and Glucose Intolerance of Aging." Diabetes (2002): 2951-2958; Gan, S K, Kriketos, A D, Poynten, A M, Furler, S M, Thompson, C H, Kraegen, E W, Campbell, L V and Chisholm, D J. "Insulin Action, Regional Fat, and Myocyte Lipid: Altered Relationships with Increased Adiposity." Obesity Research (2003): 1295-1305; Gaudet, G., Vohl, M-C, Perron, P, Tremblay, G, Gagne, C, Lesiege, D, Bergeron, J, Moorjani, S, Després, J-P. "Relationships of Abdominal Obesity and Hyperinsulinemia to Angiographically Assessed Coronary Artery Disease in Men With Known Mutations in the LDL Receptor Gene." Circulation (1998): 871-877; Goldberg, C. "'Visceral' fat removal prompts hope." Boston Globe 17 Apr. 2004: n.p. 13. Gower, B A, Munoz, J, Desmond, R, Hilario-Hailey, T and Jiao, X. "Changes in Intra-abdominal Fat in Early Postmenopausal Women: Effects of Hormone Use." Obesity Research (2006): 1046-1055; Hamdy, O. "The Role of Adipose Tissue as an Endocrine Gland." Current Diabetes Reports (2005): 317-319; Janssen, I., Katzmarzyk, P T, Ross, R, Leon, A S, Skinner, J S, Rao, D C, Wilmor, J H, Rankinen, T and Bouchard, C. "Fitness Alters the Associations of BMI and Waist Circumference with Total and Abdominal Fat**." Obesity Research (2004): 525-537; Kelley, D E and Goodpaster, B H. "Review Article, Skeletal Muscle Trigliceride, an Aspect of Regional Adiposity and Insulin Resistance." Diabetes Care (2001): 933-941; Lemieux, I, Pascot, A, Couillard, C, Lamarche, B, Tchernof, A, Almeras, N, Bergeron, J, Gaudet, D, Tremblay, G, Prud'homme, D, Nadeau, A and Despres, J-P. "Hypertriglyceridemic Waist: A Marker of the atherogenic metabolic triad (hyperinsulinemia; hyperapoliprotein B; Small, dense LDL) in Men?" Circulation (2000): 79; Mass General Hospital. "Growth Hormone Reduces Abdominal Fat, Cardiovascular Risk in HIV Patients on Antiviral Therapy." ScienceDaily 6 Aug. 2008: n.p; Moghaddam, E, Vogt, J A and Wolever, T M S. "The Effects of Fat and Protein on Glycemic Responses in Nondiabetic Humans Vary with Waist Circumference, Fasting Plasma Insulin, and Dietary Fiber Intake 1." American Society for Nutrition (2006): 2506-2511; Norstrom, A, Neovius, M G, Rössner, S and Nordstrom, P. "Postpubertal Development of Total and Abdominal Percentage Body Fat: An 8-Year Longitudinal Study." Obesity (2008): n.p; O'Connor, K G, et al. "Interrelationships of spontaneous growth hormone axis activity, body fat, and serum lipids in healthy elderly women and men." Metabolism, Clinical and Experimental (1999): 1424-1431; Pedersen S B, Borglum J D, Schmitz O, Bak J F, Sørensen N S, Richelsen B. "Abdominal obesity is associated with insulin resistance and reduced glycogen synthetase activity in skeletal muscle." Metabolism (1993): 998-1005; Pitombo, C, Araujo, E P, DeSouza, C T, Parja, J C, Beloneze, B and Velloso, L A. "Amelioration of diet-induced diabetes mellitus by removal of visceral fat." Journal of Endocrinology (2006): 699-706; Pontiroli A Pizzocri P, Librenti M. "Laparascopic adjustable gastric banding for the treatment of morbid (grade 3) obesity and its metabolic complications: a three-year study." J. Clin. Endocrinol. Metab. (2002): 3555-3561; Pories W J, Swanson M S, MacDonald K G, et al. "Who would have thought it? An operation proves to be the most effective therapy for adult-onset diabetes mellitus." Ann Surg (1995): 339-352; Schauer, P R. "Effect of Laparoscopic Roux-En Y Gastric Bypass on Type 2 Diabetes Mellitus." Annals of Surgery (2003): 467-485; Shi, H, Strader, A D, Woods, S C and Seeley, R J. "The effect of fat removal on glucose tolerance is depot specific in male and female mice." American Journal of Physiology and Endocrinological Metabolism (2007): 1012-1020; Sjostrom C, Lissner L, Wedel H, et al. "Reduction in incidence of diabetes, hypertension and lipid disturbances after intentional weight loss induced by bariatric surgery: the SOS Intervention." Obes. Res. (1999): 477-484; Soodini, G R and Hamdy, O. "Obesity and Endothelial Function, Obesity and Nutrition." Current Opinion in Endocrinology & Diabetes (2004): 186-191; Thörne, A, Lönnqvist, F, Apelman, J, Hellers, G and Amer, P. "A pilot study of long-term effects of a novel obesity treatment: omentectomy in connection with adjustable gastric banding." International Journal of Obesity (2002): 193-199; Vega, G L, Adams-Huet, B, Peshock, R, Willet, D, Shah, B and Grundy, S M. "Influence of Body Fat Content and Distribution on Variation in Metabolic Risk." The Journal of Clinical Endocrinology & Metabolism (2006): 4459-4466; Yeager, J A Florence and B F. "Treatment of Type 2 Diabetes Mellitus." American Family Physician (1999): 2049; and Yeckel, C W, Dziura, J and DiPietro, L. "Abdominal Obesity in Older Women: Potential Role for Disrupted Fatty Acid Reesterification in Insulin Resistance." Journal of the Clinical Endoctrinology and Metabolism (2008): 1285-1291.

There remains a need to effectively and safely remove large amounts of omentum while addressing the risks associated with highly vascularized hormonally active tissue.

SUMMARY OF THE INVENTION

The present invention pertains to the use of a laparoscopic and/or a natural orifice surgery ("NOSCAR") procedure to remove large amounts of omental fat from within the abdomen while addressing the complications that often arise from the highly vascularized omentum tissue that leads to excessive bleeding. In one variation, the method and system comprise a series of disposable elements that are deployed with or through an endoscope or laparoscope, primarily for securing sections of omental fat tissue, sealing the blood vessels to prevent bleeding. The system and method can include performing the procedure through a natural orifice such as the nose or mouth. In such a case, the procedure creates an opening in the stomach (thereby leaving no external visible scar). Then sections of omentum are then excised and brought into the stomach for removal. In additional variations, the omentum is drawn into the stomach and then a device is used to extract the section of omentum while cauterizing or coagulating vessels in the remaining omentum section to stem bleeding. The omentum can be macerated and evacuating from the stomach or from the abdominal cavity. One significant benefit is that the removal of significant amounts of omentum in such a minimally invasive manner provide for direct and immediate weight loss (up to 30 pounds). Moreover, because the omentum is hormonally active tissue or fat, removing this tissue from the body can reduce the incidence of morbidity from diabetes, heart disease and stroke, in obese patients. The removed omental fat can also be used for other procedures (i.e. cosmetic), as it has been shown to be more permanent than injected liposuction fat. More importantly, removal of this tissue from the body during the procedure eliminates the collateral effects of leaving the hormonal omental tissue within the body (as in such cases where the omental tissue is treated, ablated, or otherwise inactivated).

In one variation, the systems and methods described herein focuses on removing omentum and omental fat (hereafter either or both being referred to as "omental tissue") from the middle of the abdomen. Such removal can occur in an open procedure, or a minimally invasive procedure.

The methods and devices described herein permit removal of large amounts of omental fat while performing a minimally invasive and/or scar-less procedure. Moreover, the ability to secure and coagulate the omentum tissue (omentum and the omental fat) reduces the incidence of bleeding lowering the difficulty of the procedure. The ability to remove large amounts of omentum tissue also provides immediate weight loss and sculpting like liposuction.

The methods described herein include removing a portion of omentum tissue from a human body. The methods can be performed via open surgical procedures, through ports or openings in the outer abdominal wall, and/or through natural body openings such as the nose, mouth, etc.

In one variation, the method includes drawing a portion of the omentum tissue from an abdominal cavity through an incision in the body to secure the portion of omentum; separating the portion of omentum tissue from the human body while cauterizing or coagulating the portion of omentum tissue to reduce bleeding; removing the separated portion of omentum tissue from the body.

In an additional variation, the method includes removing a portion of omentum tissue from a human body by drawing a portion of the omentum tissue from an abdominal cavity to form the portion of tissue into an elongated shaped portion of tissue; separating the elongated shaped portion of tissue from the human body by cutting the elongated shaped portion of tissue; cauterizing or coagulating the elongated shaped portion of tissue to reduce bleeding; and removing the elongated shaped portion tissue from the body.

As discussed herein, separating and cauterizing or coagulating occurs simultaneously. By doing so, the physician can address the excessive bleeding risks associated with the highly vascularized omentum tissue.

Drawing of the omentum tissue through the incision can be performed mechanically, or using a vacuum-assisted grasper.

The methods include making the incision in an outer abdominal wall of the body or through internal organs. In the latter case, the incision in the internal organ should allow for accessing the abdominal cavity without creating excessive or any external scars. In one such example, drawing the portion of the omentum tissue through the incision comprises advancing an access device into a stomach of the body, creating the incision in the stomach and advancing a tissue retrieval device through the incision to draw the portion through the incision. In any case, the procedure can include the use of any number of trocars, access ports, or access catheters to facilitate passage of the devices through the incision.

The procedures described herein can be performed blindly or under direct or indirect visualization. For example, the methods can include placing a visualizing device into the abdominal cavity.

Additional variations of the invention include using a device that morselizing the portion of omentum tissue after or during drawing the portion of omentum tissue. For example, such a device can comprise a grinder or auger type mechanical system that reduces the tissue for ease of removal.

In order to facilitate separation and removal of the omentum tissue, the methods can include placing the portion of omentum tissue in a state of traction.

The method can further include drawing the portion of omentum tissue by advancing a retrieval device through the incision, where the retrieval device comprises a distal end, securing the portion of omentum tissue to the distal end and at least partially drawing the portion of omentum tissue into the distal end.

As shown, a variation of the method can include the use of a retrieval device having an expandable distal end where the expandable distal end is expanded after passing through the incision (thus reducing the size of the incision). The device can then be expanded to assist in securing the portion of omentum tissue to the distal end.

The devices described herein can include any number of an energy sources coupleable to the device to apply energy to the portion of omentum to separate and cauterize or coagulate the portion of the omentum tissue. Such energy means can include RF energy, coherent light, incoherent light, resistive heat, compressed gas, cooling fluid.

Although the disclosure discusses creation of an incision through the stomach, the method can include creation of an incision through any accessible organ within the abdominal cavity. For example such organs can include the colon, uterus, small intestine and large intestine.

In addition to the removal of omental tissue, the methods and devices described herein can also remove other tissues. For example, the methods and devices can remove abdominal fat, visceral fat, and abnormal tissue through the incision.

Variations of the devices and procedures described herein include combinations of features of the various embodiments or combination of the embodiments themselves wherever possible.

BRIEF DESCRIPTION OF THE DRAWINGS

The invention will now be described in greater detail with reference to the embodiments illustrated in the accompanying drawings, in which like elements bear like reference numerals and wherein.

DETAILED DESCRIPTION OF VARIOUS EMBODIMENTS

Figure 1A:
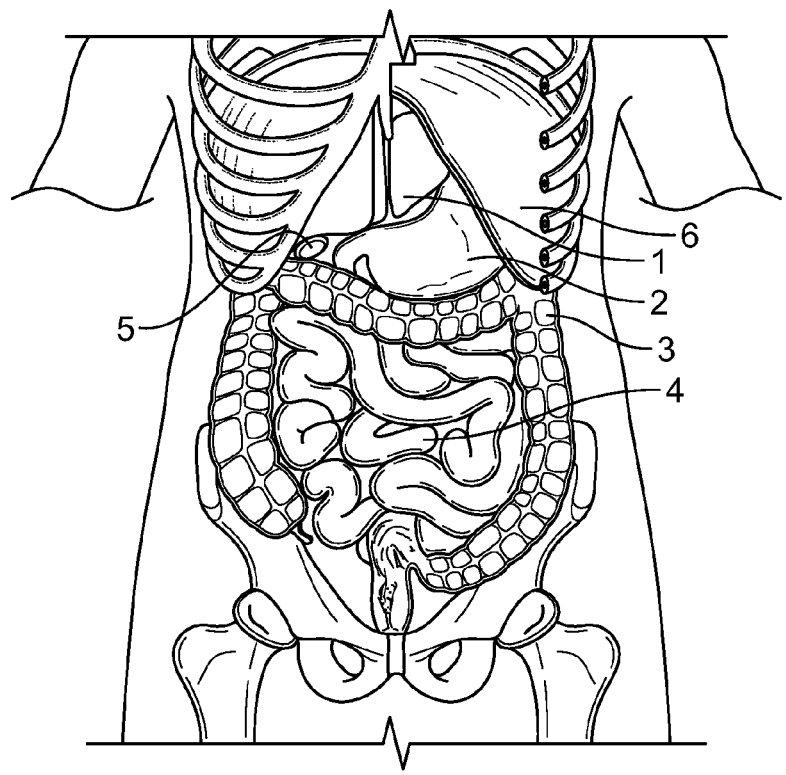
FIG. 1A illustrates an example of an abdominal cavity and abdominal organs.
Figure 1B:
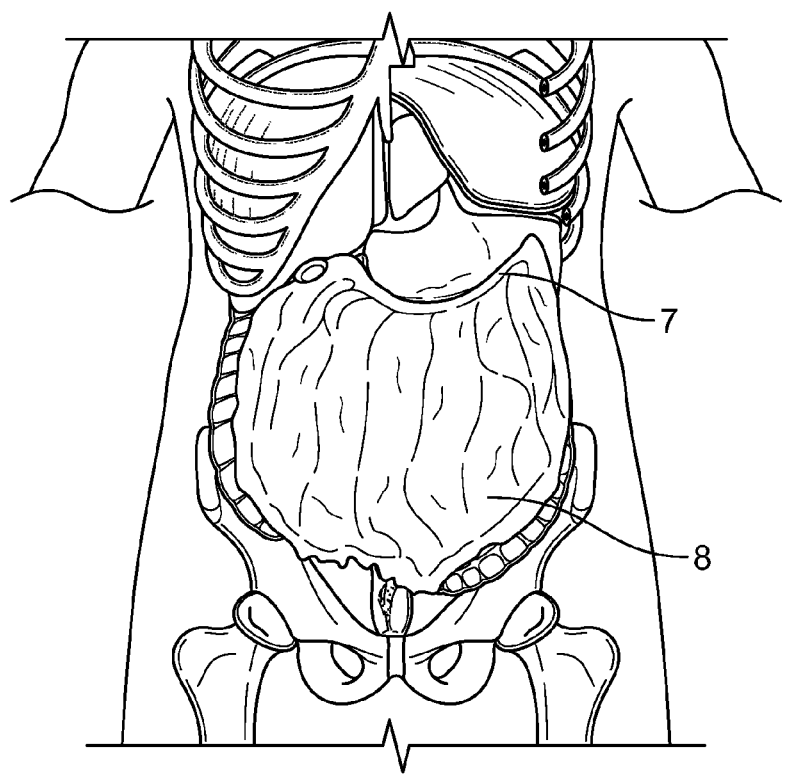
FIG. 1B illustrates an example of the omentum covering organs in the abdominal cavity.

FIG. 1A illustrates an example of an abdominal cavity and abdominal organs (including the liver 1, stomach 2, large intestines 3 and small intestines 4, as well as the gall bladder 5). As shown, the organs are located under the diaphragm 6. For purposes of illustration, the omentum and omental fat are not illustrated in the figure. However, FIG. 1B illustrates the omentum 7 and omental fat 8 which surround the abdominal organs.

Figure 2:
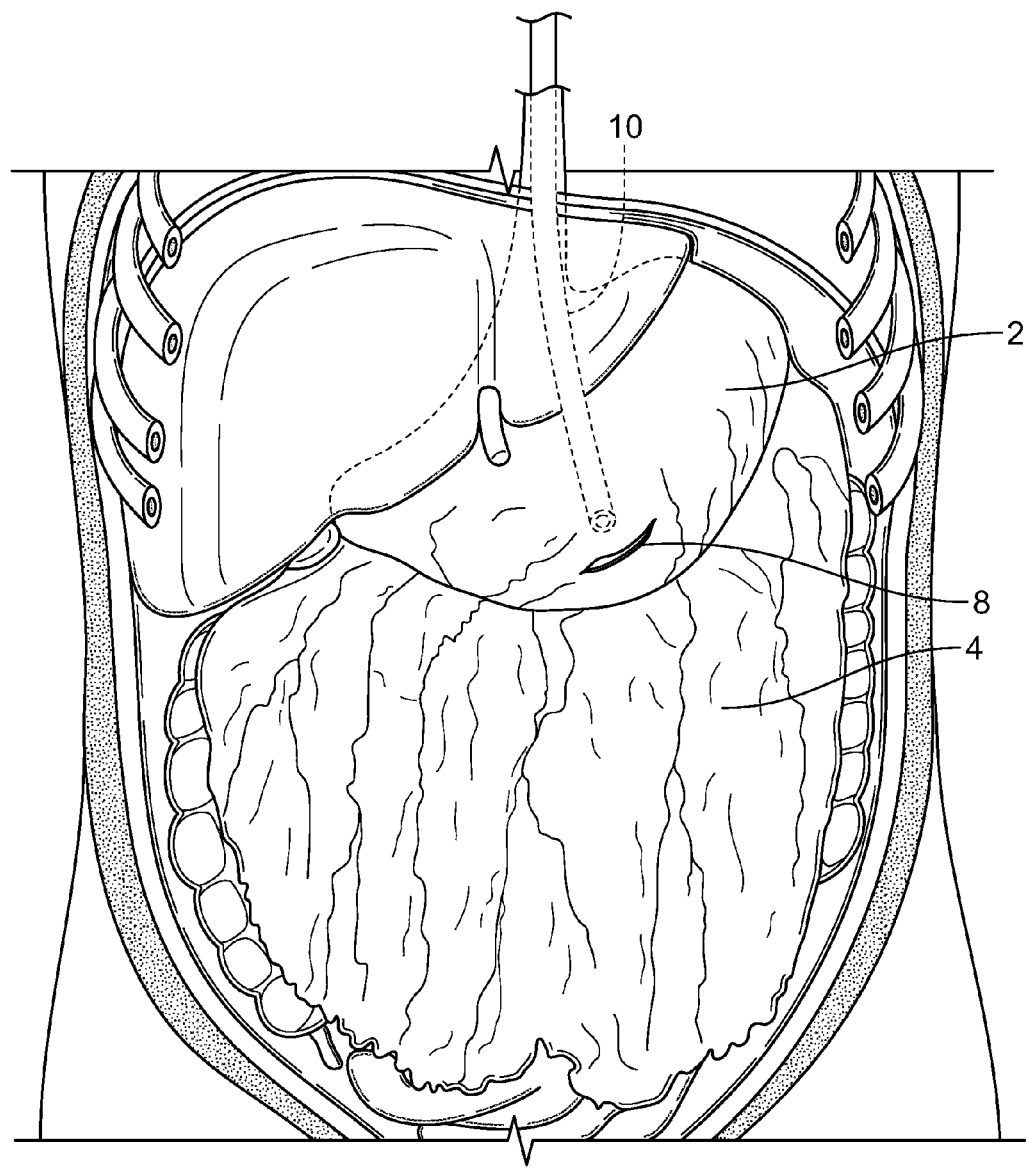
FIG. 2 illustrates the advancement of a device into the stomach to provide access to the abdominal cavity and omentum through an incision in the stomach.

In one variation, the methods described herein allow the surgeon to access the omentum and omental fat through a NOSCAR keyhole through the stomach wall. In doing so, an endoscope or other catheter can be introduced through the mouth for advancement into the stomach. The physician then makes an incision in the stomach or esophagus to enter the abdominal cavity. For example, as shown in FIG. 2, a process of removing portions of the omentum and omental fat uses a path through the stomach 2. As shown, a device 10 such as a scope or other catheter can be advanced through a natural orifice and into the stomach 2. Once inside the stomach 2 cavity, an incision or opening 8 can be made in the stomach wall to expose the omentum 4. The size of the opening 8 in the illustration is for exemplary purposes only as the size can vary as needed. The patient can be sedated, or under general anesthesia depending upon the preference of the physician and the duration of the procedure.

Figure 3A:
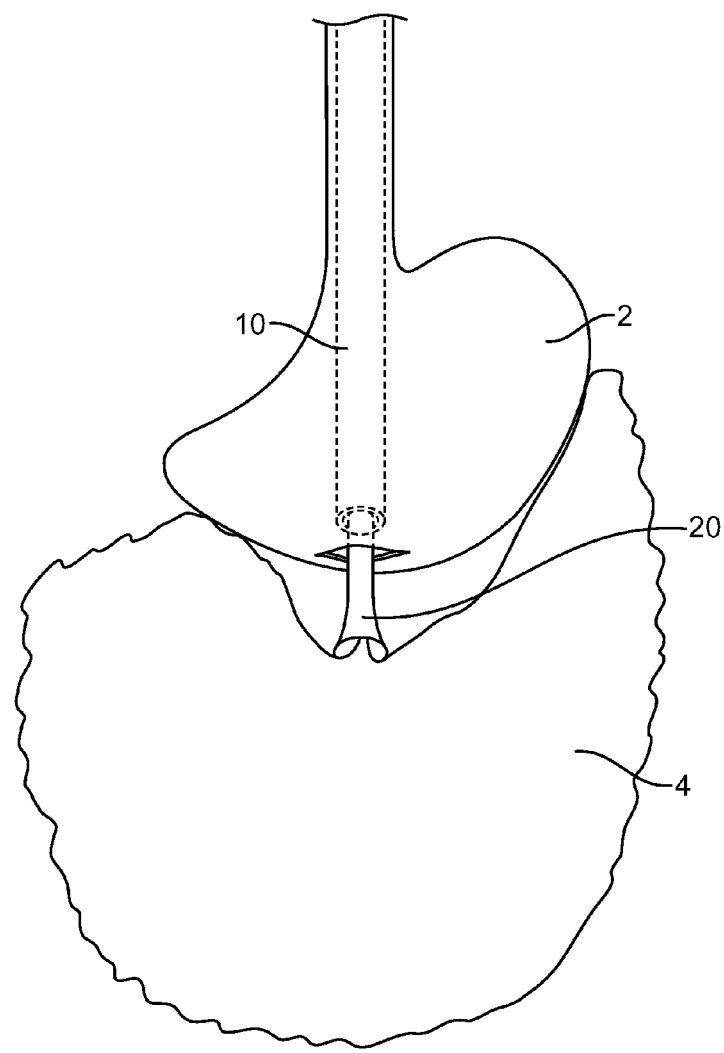
FIG. 3A illustrates an example of an omentum retrieval device advanced through an opening in the stomach to accumulate omentum tissue for resection.
Figure 3B:
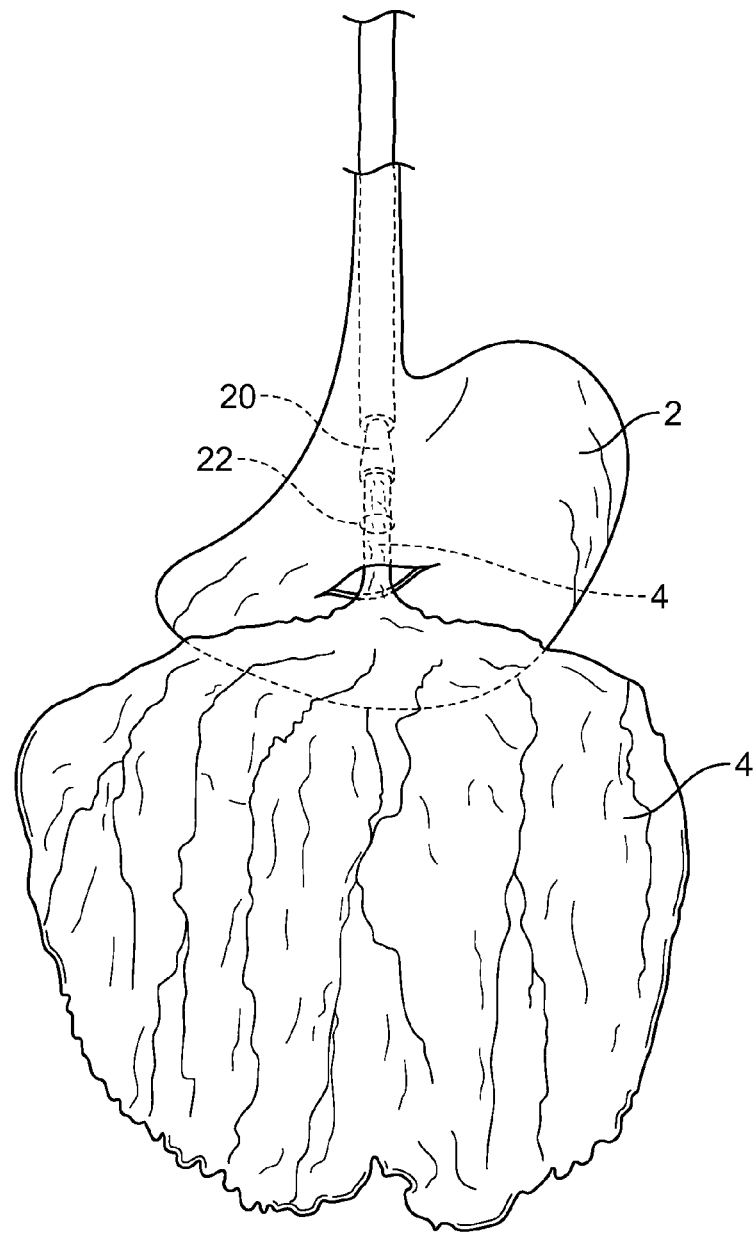
FIG. 3B illustrates withdrawing the omentum into the stomach for removal of the tissue.

Once the abdomen is accessible (i.e., via an opening in the stomach, a port that provides access to the abdomen, or via an open surgical procedure), the physician inserts a device 20 to secure the omentum 4 and omental fat. As shown in FIG. 3A, suction can be used to secure the omentum to the device 20. The cone-shaped tip compresses/groups the omentum 4 as it secures the tissue. Next, the device 20 can be withdrawn into the stomach 2 thereby pulling the omentum 4 into the stomach as shown in FIG. 3B where it can be separated from the remaining omentum tissue and where the vessels in the severed omentum tissue can be cauterized or coagulated. In the illustrated variation, an electrosurgical loop 22 is advanced over the device 20 so that a cutting loop encircles the compressed and drawn omentum 4. The electrosurgical loop is then activated to sever the omentum 4 as well as coagulate any open blood vessels. The omentum debris is then aspirated through the device and retained for further use, or disposed. In any event, the severed omentum tissue is removed from the body. In an alternative variation, the omentum tissue can be severed from the remaining omentum portion outside of the stomach.

In one variation of the methods and system, the distal end of the omentum retrieval/securing device 20 comprises an expandable shape. Therefore, the device 20 is capable of being inserted through the lumen of a laparoscopic introducer such as an 8 mm introducer, or though the working channel of an endoscope. After introduction, through hole having a minimum dimension to accommodate the device 20, the distal end of the device 20 expands improve its ability to draw tissue into the device for removal from the body.

Although the above example shows an electrosurgical means for severing and coagulating, any similar device can be employed. For example, the tissue securing device can include heating to seal the blood vessels using radiofrequency energy, lower frequency electrical energy, resistive heating, compression, freezing, cooling, a combination of any of these. Moreover, such coagulation modes can be combined with mechanical cutting, grinding, and/or shredding to remove the omentum tissue.

As noted herein, while variations of the method and system include accessing the abdominal cavity via the stomach, the methods can be supplemented by the use of one or more ports in an abdominal wall. Alternatively, the procedure can take place entirely via ports in the abdomen. In any case, in these variations, the procedure is performed without leaving any long skin incisions. However, additional variations of the method also include removal of the omental fat via an open surgical procedure.

Figure 4:
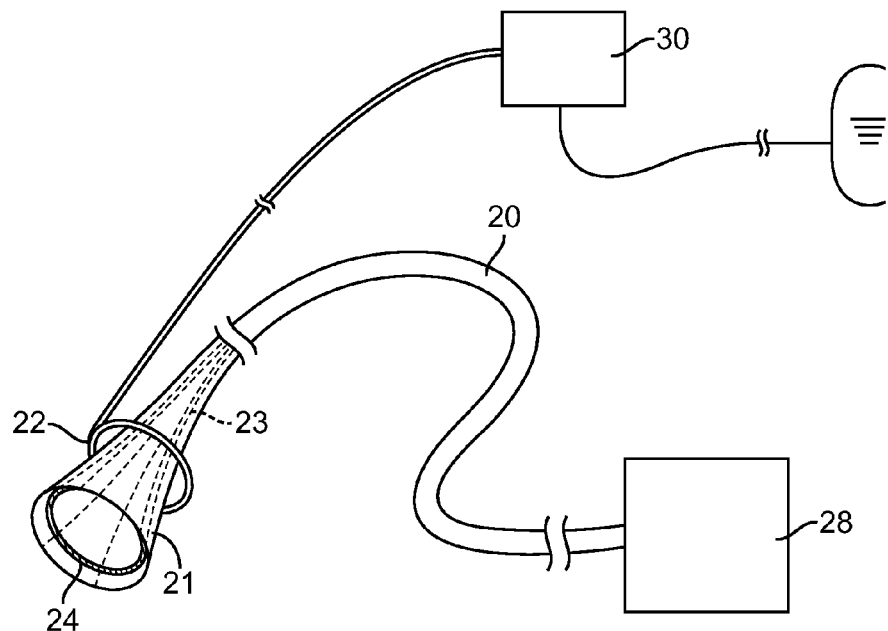
FIG. 4 illustrates an example of a device for retrieving and removing omentum tissue.
Figure 5:
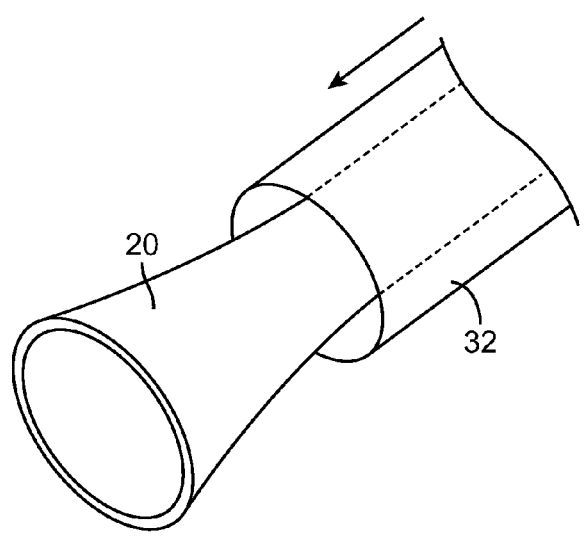
FIG. 5 illustrates a variation of a device of FIG. 4 further including a restraining conduit.

FIG. 4 shows one example of a variation of a device 20 for use as described herein. As shown, the device 20 can include an expandable distal end 21. The expandable end allows creation of a small opening in tissue to perform the procedure. Furthermore, the device 20 is coupled to a vacuum source 28 to pull tissue through the distal end 21. Accordingly, the retrieval device 20 can include one or more valves 23 (as shown in FIG. 3A) to regulate the vacuum applied through the device. As noted above, the distal end 21 can optionally compress the omentum tissue.

Alternatively, the device 20 can secure the omentum tissue so that upon withdrawal of the device 20 a strand or section of omentum is pulled along as the device is withdrawn. As also shown, the device 20 can be coupled to an energy source 30 that includes an optional ground plate 26 (for those variations that are mono-polar). In another variation, the omentum securing device 20 can include a return electrode within or about the distal end 21. In this latter variation, the presence of a return electrode on the device 20 distal end 21 permits a shorter conduction path between electrodes and improves cutting and coagulation of the omentum at lower power consumption. The omentum securing device 20 can further include a vacuum pump 28 to produce suction through securing device 20 to bring tissue material into the distal end of the device. The pump can include a pressure gauge to indicate tissue contact and to allow the physician to control the force of suction delivered to the tissue.

The flared end 21 of the retrieval device 20 can be self expanding. For example, the flared end 21 can include one or more shape setting splines or supports 23 located a the distal end where advancement of the distal end 21 from the endoscope causes the splines to urge outward to expand the flared end. The splines 23 can be molded as part of the distal end 21 or otherwise attached can be made out of memory metal alloy or polymer or can be structurally stiff by altering the durometer of the polymer and the shape such that when constrained, the flare is reduced and when released, the flare is spread. The device 20 can also include a restraining conduit 32 that compresses the flared end 21 by advancing distally over the flared portion.

Figure 6:
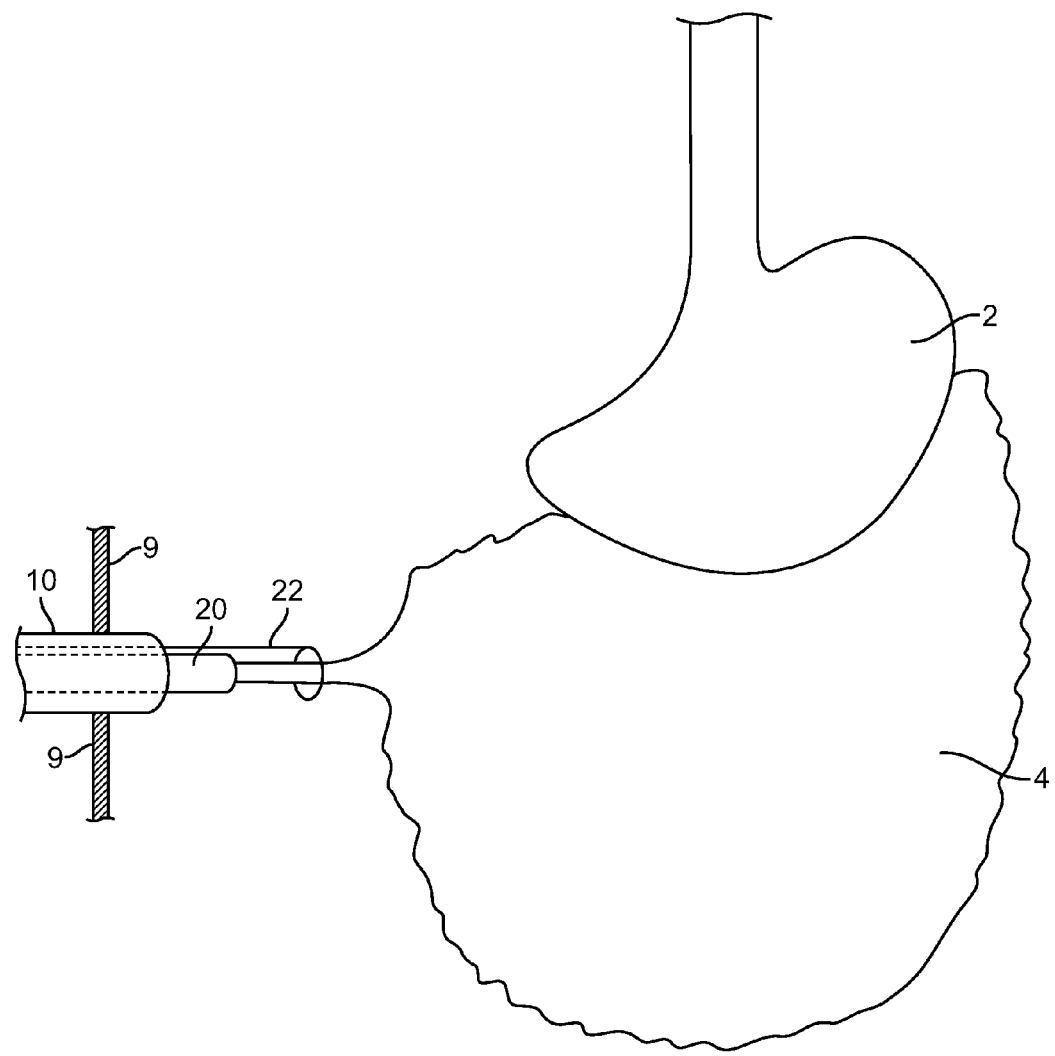
FIG. 6 illustrates a variation of removing omentum by compressing and drawing the omentum tissue within the abdominal cavity or through an abdominal wall.

FIG. 6 illustrates another variation of an omentum retrieval device 20. In this variation, the device 20 is advanced through a scope or port 10 that is placed through a wall 9 of the abdomen. The device secures the omentum tissue 4 and draws or compresses the tissue so that the secured tissue can be cut and coagulated with an electrosurgical or other device 22. The tissue debris is then removed from the body via device 20.

What is claimed is:

1. A method of removing a portion of omentum tissue from a human body, the method comprising:
    drawing a portion of the omentum tissue from an abdominal cavity through an incision in the body;
    separating the portion of omentum tissue from the human body while applying energy to the portion of omentum tissue to reduce bleeding; and
    removing the separated portion of omentum tissue from the body.

2. The method of claim 1, where drawing the portion of the omentum tissue through the incision comprises securing the portion with a vacuum-assisted grasper.

3. The method of claim 1, where drawing the portion of the omentum tissue through the incision comprises advancing an access device into a stomach of the body, creating the incision in the stomach and advancing a tissue retrieval device through the incision to draw the portion through the incision.

4. The method of claim 1, where the incision is created in an abdominal wall.

5. The method of claim 1, further comprising placing a trocar or access port through the incision.

6. The method of claim 1, further comprising placing a visualizing device into the abdominal cavity.

7. The method of claim 1, where applying energy to the portion of the omentum tissue comprises heating or cooling the omentum tissue.

8. The method of claim 1, further comprising morselizing the portion of omentum tissue after or during drawing the portion of omentum tissue.

9. The method of claim 1, where separating the portion of omentum tissue is performed by a process selected from the group consisting of heating and mechanically cutting the portion of tissue.

10. The method of claim 1, where drawing the portion of omentum tissue comprises placing the portion of omentum tissue in a state of fraction.

11. The method of claim 1, where removing the separated portion of omentum tissue from the body comprises applying a vacuum to the portion of omentum tissue.

12. The method of claim 1, where drawing the portion of omentum tissue comprises advancing a retrieval device through the incision, where the retrieval device comprises a distal end, securing the portion of omentum tissue to the distal end and at least partially drawing the portion of omentum tissue into the distal end.

13. The method of claim 12, further advancing an electrosurgical component over the drawn portion of omentum tissue, where separating the portion of omentum tissue comprises applying energy through the electrosurgical component.

14. The method of claim 12, where the distal end of the retrieval device is expandable, and further comprising expanding the distal end prior to securing the portion of omentum tissue to the distal end.

15. The method of claim 14, further comprising compressing the distal end with an overtube to secure the portion of omentum tissue within the distal end.

16. The method of claim 12, further comprising applying a vacuum through the retrieval device to secure the portion of omentum tissue to the distal end.

17. The method of claim 16, where the retrieval device further includes a valve, and where applying the vacuum through the retrieval device further comprising applying actuating the valve to apply the vacuum.

18. The method of claim 12, where the device further includes an energy source coupleable to the device to apply energy to the portion of omentum to separate and cauterize or coagulate the portion of the omentum tissue.

19. The method of claim 18, where the energy source comprises an energy source selected from the group consisting of RF energy, coherent light, incoherent light, resistive heat, compressed gas and cooling fluid.

20. The method of claim 1, where the incision is made in an organ selected from the group consisting of the colon, uterus, small intestine and large intestine.

21. The method of claim 1, further comprising removing abdominal fat, visceral fat, and abnormal tissue through the incision.

22. The method of claim 1, where separating and applying energy occurs simultaneously.

23. A method of removing a portion of omentum tissue from a human body, the method comprising:
    drawing a portion of the omentum tissue from an abdominal cavity to form the portion of tissue into an elongated shaped portion of tissue;
    separating the elongated shaped portion of tissue from the human body by cutting the elongated shaped portion of tissue;
    applying energy to the elongated shaped portion of tissue to reduce bleeding; and
    removing the elongated shaped portion tissue from the body.

24. The method of claim 23, where separating and applying energy occurs simultaneously.

* * * * *